(12) United States Patent
Roy et al.

(10) Patent No.: US 11,728,040 B2
(45) Date of Patent: Aug. 15, 2023

(54) NEUROMODULATION BASED ADAPTIVE CONTROLLER FOR MITRAL STENOSIS

(71) Applicant: Tata Consultancy Services Limited, Mumbai (IN)

(72) Inventors: Dibyendu Roy, Kolkata (IN); Oishee Mazumder, Kolkata (IN); Aniruddha Sinha, Kolkata (IN); Sundeep Khandelwal, Noida (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 213 days.

(21) Appl. No.: 17/149,059

(22) Filed: Jan. 14, 2021

(65) Prior Publication Data
US 2021/0280319 A1    Sep. 9, 2021

(30) Foreign Application Priority Data

Jan. 29, 2020    (IN) .............................. 202021004023

(51) Int. Cl.
*G16H 50/50* (2018.01)
*G16H 20/30* (2018.01)
(Continued)

(52) U.S. Cl.
CPC ............. *G16H 50/50* (2018.01); *G16H 20/30* (2018.01); *G16H 40/67* (2018.01); *G16H 50/70* (2018.01); *G16H 70/60* (2018.01); *A61N 1/36114* (2013.01)

(58) Field of Classification Search
CPC ........ G16H 50/00; G16H 50/50; G16H 50/70; G16H 70/00; G16H 70/60; G16H 20/30; G16H 20/10; G16H 40/67
USPC .......................................................... 705/2
See application file for complete search history.

(56) References Cited

U.S. PATENT DOCUMENTS

| 4,429,701 A * | 2/1984 | Goor ................. A61B 5/02158 600/526 |
| 8,295,907 B2 | 10/2012 | Sun et al. |
| 2002/0022785 A1* | 2/2002 | Romano .............. A61B 5/7239 600/526 |

FOREIGN PATENT DOCUMENTS

| WO | WO-0064339 A1 * | 11/2000 | ............. A61B 5/029 |
| WO | WO-2010059291 A1 * | 5/2010 | ......... A61B 5/02007 |
| WO | WO-2017100188 A2 * | 6/2017 | ........... A61B 5/0024 |

OTHER PUBLICATIONS

Coulson, Alan S; Right thoracotomy approach to mitral valve surgical procedures; AORN Journal 65.n2: p345(20). Association of Operating Room Nurses, Inc. (Feb. 1997). (Year: 1997).*

(Continued)

*Primary Examiner* — Hiep V Nguyen
(74) *Attorney, Agent, or Firm* — Finnegan, Henderson, Farabow, Garrett & Dunner, L.L.P.

(57) ABSTRACT

This disclosure provides a simulation platform to study and perform predictive analysis on valvular heart disease, Mitral stenosis (MS) and provides a control approach to correct hemodynamic imbalances during MS conditions. Conventional approaches of valve repair or replacement are often associated with risk of thromboembolism, need for anticoagulation, prosthetic endocarditis, and impaired left ventricle function. The cardiovascular hemodynamics model of the present disclosure helps to create 'what if' conditions to study variations in different hemodynamic parameters like blood flow, aortic and ventricular pressure, etc. during normal and pathological conditions. An adaptive control system in conjunction with the hemodynamic cardiovascular system (CVS) is provided to handle hemodynamic disbalance during moderate to severe MS conditions. The adaptive controller is hypothesized in line with the neuromodulation approach and modulates left ventricular contractility and vagal tone to counter the symptoms associated with MS.

13 Claims, 11 Drawing Sheets

(51) Int. Cl.
  *G16H 40/67* (2018.01)
  *G16H 70/60* (2018.01)
  *G16H 50/70* (2018.01)
  *A61N 1/36* (2006.01)

(56) References Cited

OTHER PUBLICATIONS

Menon Gopalakrishna, Prahlad; Medical Device Design for Improved Cardiopulmonary Bypass Perfusion and Hemodynamic Optimality during Cardiovascular procedures using Image-Based Computational Fluid Dynamics; Carnegie Mellon University. ProQuest Dissertations Publishing, 2013. 3573505. (Year: 2013).*

Faragallah et al., "A New Control System for Left Ventricular Assist Devices Based on Patient-Specific Physiological Demand," Inverse Problems in Science and Engineering, 20:5-6 (2012).

King et al., "Finite state machine implementation for left ventricle modeling and control," BioMed Eng OnLine, 18:10 (2019).

Paeme et al., "Mathematical multi-scale model of the cardiovascular system including mitral valve dynamics. Application to ischemic mitral insufficiency," BioMedical Engineering OnLine, 10:86 (2011).

Scarsoglio et al., "Computational fluid dynamics modelling of left valvular heart diseases during atrial fibrillation," PeerJ 4:e2240 (2016).

Son et al., "Stochastic Modeling and Dynamic Analysis of the Cardiovascular System with Rotary Left Ventricular Assist Devices," Mathematical Problems in Engineering, Article ID: 7179317, 18 pages (2019).

* cited by examiner

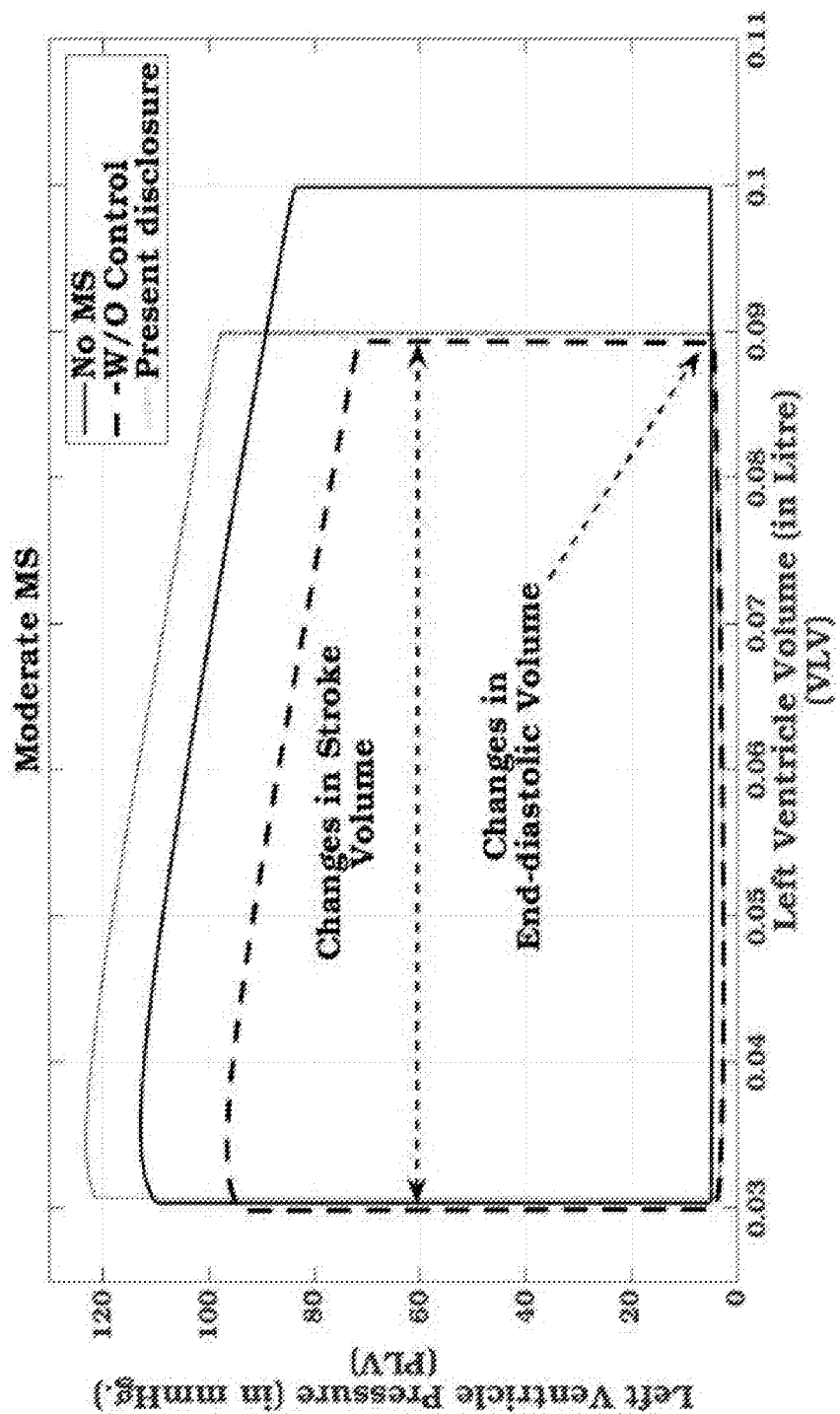

NEUROMODULATION BASED ADAPTIVE CONTROLLER FOR MITRAL STENOSIS

PRIORITY CLAIM

This U.S. patent application claims priority under 35 U.S.C. § 119 to: Indian Patent Application No. 202021004023, filed on 29 Jan. 2020. The entire contents of the aforementioned application are incorporated herein by reference.

TECHNICAL FIELD

The disclosure herein generally relates to a cardiovascular model with mitral insufficiency, and, more particularly, to predictive analysis of Mitral Stenosis (MS) and control approach to correct associated hemodynamic imbalances.

BACKGROUND

Valvular heart disease (VHD) is an important cause of cardiovascular morbidity and mortality worldwide, affecting aging population by degenerative valve disease and the younger population by rheumatoid related valve disorders. Moderate to severe Mitral Stenosis (MS) accounts for a majority of VHD diagnoses in terms of health care burden and prevalence along with Mitral Regurgitation (MR) and Aortic Stenosis (AS). The mitral valve is a complex system integrated inside the left ventricle (LV), including the ventricle itself along with papillary muscles, annulus, leaflets and chordae. This valve plays a fundamental role in the structural and functional integrity of the LV, along with maintaining forward cardiac output. Normal mitral valve performance requires chordae tendinae and papillary muscles of appropriate size and position with thin, mobile leaflets. Dysfunction arising due to structural defects in any of the valve structures may result in symptoms like reduced cardiac output, pulmonary venous congestion, and atrial arrhythmia.

Although surgical replacement of the valve through the prosthetic valve is the conventional approach of treatment, replacement is often associated with risk of thromboembolism, need for anticoagulation, prosthetic endocarditis, and impaired LV-function. Valve 'repairing technique' is an alternative known in the art approach. For example, catheter-based balloon valvuloplasty is a primary therapeutic option for mitral stenosis, while Transcatheter mitral valve implantation (TVMI) is a potential therapeutic option for patients who are not eligible for valve repair due to severe anatomical and functional abnormalities. However, valve replacement and repair are complementary rather than competitive in current surgical practice. A multi-center randomized trial comparing valve repair to valve replacement, by T. F. Luscher in a publication entitled "*Mitral valve disease, atrial fibrillation, and device therapy*" did not observe significant differences in LV reverse remodeling or survival.

SUMMARY

Embodiments of the present disclosure present technological improvements as solutions to one or more of the above-mentioned technical problems recognized by the inventors in conventional systems.

In an aspect, there is provided a processor implemented method for enhancing cardiac output (CO) in a subject having Mitral Stenosis (MS), the method comprising the steps of: receiving, via one or more hardware processors serving as a first controller, an error e1 between an actual left ventricular pressure $P_{lv}$ from a hemodynamic cardiovascular system (CVS) model representative of the subject having MS and a desired left ventricular pressure $P_{lv}^d$, wherein the desired left ventricular pressure corresponds to a healthy cardiovascular system; generating an updated left ventricle end diastolic compliance $\tilde{c}_{lv,d}$ via the first controller, by minimizing the error e1; receiving, via one or more hardware processors serving as a second controller, an error e2 between an actual aortic pressure $P_{sa}$ from the hemodynamic CVS model and a desired aortic pressure $P_{sa}^d$, wherein the desired aortic pressure corresponds to the healthy cardiovascular system; generating an updated systemic vascular resistance $\tilde{R}_s$, via the second controller, by minimizing the error e2; receiving, via one or more hardware processors serving as a third controller, the updated left ventricle end diastolic compliance $\tilde{c}_{lv,d}$ and the updated systemic vascular resistance $\tilde{R}_s$ to generate control inputs $u_1$ and $u_2$ for opening and closing a mitral valve and an aortic valve respectively; and receiving, via the hemodynamic CVS model, the updated left ventricle end diastolic compliance $\tilde{c}_{lv,d}$, the updated systemic vascular resistance $\tilde{R}_s$ and the generated control inputs $u_1$ and $u_2$; wherein the $\tilde{c}_{lv,d}$ and the $\tilde{R}_s$ represent parameters that are adaptively controlled by neuromodulation for enhancing the CO in the subject having MS.

In another aspect, there is provided a system for enhancing cardiac output (CO) in a subject having Mitral Stenosis (MS), the system comprising: one or more data storage devices operatively coupled to one or more hardware processors and configured to store instructions configured for execution via the one or more hardware processors serving as a first controller, a second controller, a third controller and a hemodynamic cardiovascular system (CVS) model representative of the subject having MS to: receive via the first controller, an error e1 between an actual left ventricular pressure $P_{lv}$ from the hemodynamic CVS model and a desired left ventricular pressure $P_{lv}^d$, wherein the desired left ventricular pressure corresponds to a healthy cardiovascular system; generate an updated left ventricle end diastolic compliance $\tilde{c}_{lv,d}$ via the first controller, by minimizing the error e1; receive via the second controller, an error e2 between an actual aortic pressure $P_{sa}$ from the hemodynamic CVS model and a desired aortic pressure $P_{sa}^d$, wherein the desired aortic pressure corresponds to the healthy cardiovascular system; generate an updated systemic vascular resistance $\tilde{R}_s$, via the second controller, by minimizing the error e2; receive, via the third controller, the updated left ventricle end diastolic compliance $\tilde{c}_{lv,d}$ and the updated systemic vascular resistance $\tilde{R}_s$ to generate control inputs $u_1$ and $u_2$ for opening and closing a mitral valve and an aortic valve respectively; and receive, via the hemodynamic CVS model, the updated left ventricle end diastolic compliance $\tilde{c}_{lv,d}$, the updated systemic vascular resistance $\tilde{R}_s$ and the generated control inputs $u_1$ and $u_2$; wherein the $\tilde{c}_{lv,d}$ and the $\tilde{R}_s$ represent parameters that are adaptively controlled by neuromodulation for enhancing the CO in the subject having MS.

In yet another aspect, there is provided a computer program product comprising a non-transitory computer readable medium having a computer readable program embodied therein, wherein the computer readable program, when executed on a computing device, causes the computing device to: receive an error e1 between an actual left ventricular pressure $P_{lv}$ from a hemodynamic CVS model and a desired left ventricular pressure $P_{lv}^d$, wherein the desired left ventricular pressure corresponds to a healthy cardiovascular system; generate an updated left ventricle end diastolic compliance $\tilde{c}_{lv,d}$, by minimizing the error e1; receive an error e2 between an actual aortic pressure $P_{sa}$ from the hemodynamic CVS model and a desired aortic pressure $P_{sa}^d$, wherein the desired aortic pressure corresponds to the healthy cardiovascular system; generate an updated systemic vascular resistance $\tilde{R}_s$ by minimizing the error e2; receive the updated left ventricle end diastolic compliance $\tilde{c}_{lv,d}$ and the updated systemic vascular resistance $\tilde{R}_s$ to generate control inputs $u_1$ and $u_2$ for opening and closing a mitral valve and an aortic valve respectively: and receive, via the hemodynamic CVS model, the updated left ventricle end diastolic compliance $\tilde{c}_{lv,d}$ the updated systemic vascular resistance $\tilde{R}_s$ and the generated control inputs $u_1$ and $u_2$; wherein the $\tilde{c}_{lv,d}$ and the $\tilde{R}_s$ represent parameters that are adaptively controlled by neuromodulation for enhancing the CO in the subject having MS.

In accordance with an embodiment of the present disclosure the updated left ventricle end diastolic compliance $\tilde{c}_{lv,d}$ is based on the actual left ventricular pressure $P_{lv}$, a rate of change of the desired left ventricular pressure $\dot{P}_{lv}^d$, and a diastolic time duration $T-T_s$, and wherein T represents duration of a cardiac cycle having a systolic duration $T_s$, such that the $\tilde{c}_{lv,d}$ is limited to a physiological acceptable range for left ventricle end diastolic compliance $[c_{lv,d}^{min}, c_{lv,d}^{max}]$.

In accordance with an embodiment of the present disclosure, the updated left ventricle end diastolic compliance $\tilde{c}_{lv,d}$ is represented according to the equation $$\tilde{c}_{lv,d} = \begin{cases} c_{lv,d}^{max} & \text{if } \hat{c}_{lv,d} > c_{lv,d}^{max} \\ \hat{c}_{lv,d} & \text{if } c_{lv,d}^{max} \geq \hat{c}_{lv,d} \geq c_{lv,d}^{min}, \\ c_{lv,d}^{min} & \text{if } \hat{c}_{lv,d} > c_{lv,d}^{min} \end{cases}$$

and wherein $\hat{c}_{lv,d}$ is an estimated left ventricle end diastolic compliance and is represented according to the equation $$\hat{c}_{lv,d} = \exp\left(-\frac{\dot{P}_{lv}^d(t-T_s)}{P_{lv}}\right).$$

In accordance with an embodiment of the present disclosure, the updated systemic vascular resistance $\tilde{R}_s$ is based on the actual aortic pressure $P_{sa}$, a rate of change of the desired aortic pressure $\dot{P}_{sa}^d$ and a left atrial pressure $P_{la}$, such that the $\tilde{R}_s$ is limited to a physiological acceptable range for systemic vascular resistance $[R_s^{min}, R_s^{max}]$.

In accordance with an embodiment of the present disclosure, the updated systemic vascular resistance $\tilde{R}_s$ is represented according to the equation $$\tilde{R}_s = \begin{cases} R_s^{max} & \text{if } \hat{R}_s > R_s^{max} \\ R_s & \text{if } R_s^{max} \geq \hat{R}_s \geq R_s^{min}, \\ R_s^{min} & \text{if } \hat{R}_s > R_s^{min} \end{cases}$$

wherein $\hat{R}_s$ is an estimated systemic vascular resistance and is represented according to the equation $$\hat{R}_s = -\frac{P_{sa} - P_{la}}{c_{sa}\dot{P}_{sa}^d},$$

and wherein $c_{sa}$ is a constant representing a systemic vascular compliance.

In accordance with an embodiment of the present disclosure, the hemodynamic CVS model is further configured to receive a cascaded control unit u based on the control inputs $u_1$ and $u_2$, wherein the cascaded control unit $\tilde{u}$ is represented in a state space form according to the equation $$\tilde{u} = \tilde{G}^{-1}(\dot{x}^d - \tilde{A}x)\big|_{R_s=\tilde{R}_s,c_{lv,d}=\tilde{c}_{lv,d}},$$

and wherein $\dot{x} = A(t)x + G(x,t)u$,
$x = [P_{lv}\ P_{la}\ P_{sa}]^T$, $P_{la}$ representing a left atrial pressure,
$u = [u_1\ u_2]^T$,
A(t) is a state matrix represented as $$\begin{bmatrix} -\frac{\dot{c}_{lv}(t)}{c_{lv}(t)} & 0 & 0 \\ 0 & -\frac{\dot{c}_{la}(t)}{c_{la}(t)} & \frac{1}{c_{la}(t)R_s} \\ 0 & \frac{1}{c_{sa}R_s} & -\frac{1}{c_{sa}R_s} \end{bmatrix},$$

G(x,t) is an input matrix represented as $$\begin{bmatrix} \frac{P_{la}-P_{lv}}{c_{lv}(t)R_{mi}} & -\frac{P_{lv}-P_{sa}}{c_{lv}(t)R_{ao}} \\ -\frac{P_{la}-P_{lv}}{c_{la}(t)R_{mi}} & 0 \\ 0 & \frac{P_{lv}-P_{sa}}{c_{sa}R_{ao}} \end{bmatrix},$$

$x^d(t) = [P_{lv}\ P_{la}^d\ P_{sa}^d]^T$ represents a desired state corresponding to the healthy cardiovascular system, $$\tilde{A}(t) = A(t)\big|_{\tilde{R}_s,\tilde{c}_{lv,d}}, \text{ and } \tilde{G}(x,t) = G(x,t)\big|_{\tilde{c}_{lv,d}}.$$

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 6A through FIG. 6C illustrate a comparative analysis of the MS severity—Mild MS, Moderate MS and Severe MS respectively, with respect to the Left ventricle Pressure Left ventricle Volume loop (PV-loop), in accordance with some embodiments of the present disclosure.

DETAILED DESCRIPTION

Figure 1:
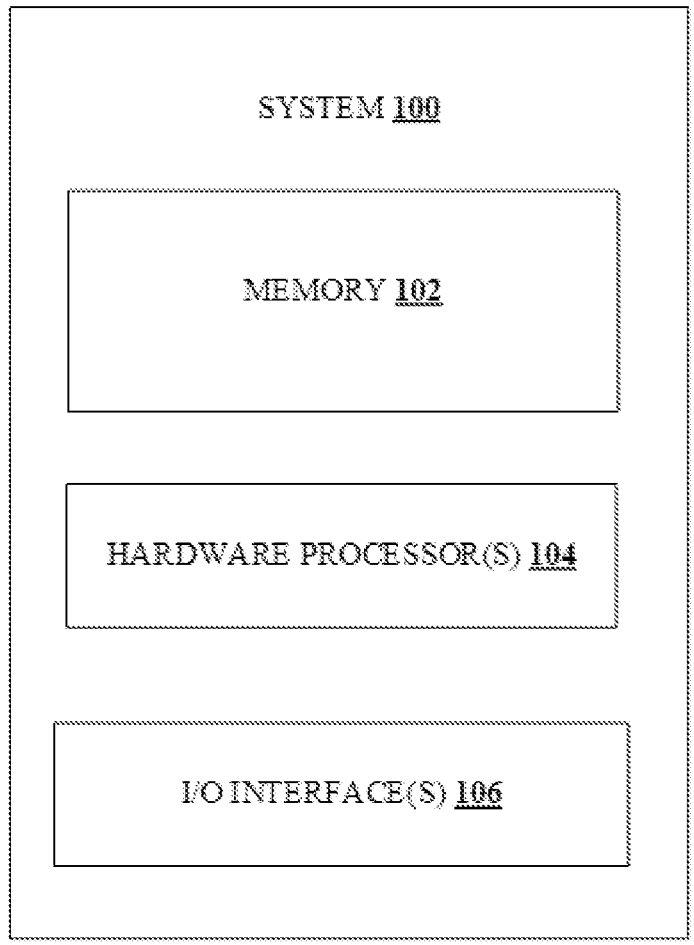
FIG. 1 illustrates an exemplary block diagram of a system for enhancing cardiac output (CO) in a subject having Mitral Stenosis (MS), in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Cardiovascular diseases (CVDs) constitute one of the most significant causes of mortality in the world as suggested by the World Health Organization (WHO) and Valvular heart disease (VHD) is a prominent cause of cardiovascular morbidity and mortality worldwide. Conventional approaches of treatment include valve repair or valve replacement is often associated with risk of thromboembolism, need for anticoagulation, prosthetic endocarditis, and impaired left ventricle function. The autonomic nervous system through its sympathetic and parasympathetic control modulates heart rate, vagal tone, contractility, and the like. Neuromodulation in the Vagal nerve has been used for the treatment of heart failure using the 'CardioFit' System disclosed by M. Kobayashi, et al. in the disclosure entitled "*Cardiac autonomic nerve stimulation in the treatment of heart failure*". It is understood that Vagal Nerve stimulation (VNS) along with its hemodynamic effects, attenuates the systemic inflammatory response and activation of the renin-angiotensin system in animal heart failure models. VNS acts to reduce elevated heart rate created by increased sympathetic tone, which in turn improves diastolic filling and coronary perfusion. These VNS effects combine to slow or reverse the progression of chronic heart failure. It is understood from research that VNS is being proposed as an adjuvant to defibrillator and resynchronization therapies, due to its powerful anti-fibrillatory effect.

The present disclosure combines the effect of VNS like neuromodulation approach and its effect in rectifying hemodynamic imbalances in MS conditions in a simulation environment. As described hereinafter, modulation of left ventricle contractility and systemic resistance is capable of stabilizing the hemodynamic imbalance created in moderate to severe MS. An adaptive controller (system 100 described later in the description) is provided to restore near-normal hemodynamic conditions.

Referring now to the drawings, and more particularly to FIGS. 1 through 9, where similar reference characters denote corresponding features consistently throughout the figures, there are shown preferred embodiments and these embodiments are described in the context of the following exemplary system and/or method.

FIG. 1 illustrates an exemplary block diagram of a system 100 for enhancing cardiac output (CO) in a subject having Mitral Stenosis (MS), in accordance with some embodiments of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

In accordance with the present disclosure, a hemodynamic cardiovascular system (CVS) model representative of the subject having MS is considered. In an embodiment, the hemodynamic CVS model is modeled as a four chambered heart along with pulmonary and systemic blood flow governed with hemodynamic equations, modeled using Simulink, Matlab™. The hemodynamic CVS model is a simplistic, lumped and reduced model of the human cardiovascular mechanism, modeled essentially to capture pressure and flow variation during normal and pathological conditions. The main components modeled are blood vessels with flow dynamics, heart chamber with contractility function and a much-simplified part of the central nervous system (CNS) regulating blood pressure, replicating Baroreflex mechanism. In an exemplary embodiment, the hemodynamic CVS model may be as disclosed in the Applicant's Application No. 201921029536 titled Method And System For Pressure Autoregulation Based Synthesizing Of Photoplethysmogram Signal In accordance with the present disclosure, it is assumed that the right heart and pulmonary circulation are healthy and normal and hence do not affect blood circulation in the left heart. Accordingly, in the hemodynamic CVS model, the right heart dynamics are not examined. Moreover, to simplify modeling, it is assumed that the blood flow through the aorta is directly coming back to the left atrium (la) through the systemic vein.

In accordance with the present disclosure, the behavior of the left atrium (la or LA) and left ventricle (lv or LV) is modeled by a time varying compliance functions and it is further assumed that there exists a certain delay (T) between the la compliance function $c_{la}(t)$ and the lv compliance function $c_{lv}(t)$.

Based on the above assumption, in an embodiment, a third order hemodynamic CVS model replicating the left heart dynamics may be expressed as:

$$\begin{bmatrix} \dot{P}_{lv} \\ \dot{P}_{la} \\ \dot{P}_{sa} \end{bmatrix} = \begin{bmatrix} -\frac{\dot{c}_{lv}(t)}{c_{lv}(t)} & 0 & 0 \\ 0 & -\frac{\dot{c}_{la}(t)}{c_{la}(t)} & \frac{1}{c_{la}(t)R_s} \\ 0 & \frac{1}{c_{sa}R_s} & -\frac{1}{c_{sa}R_s} \end{bmatrix} \begin{bmatrix} P_{lv} \\ P_{la} \\ P_{sa} \end{bmatrix} + \quad (1)$$

$$\begin{bmatrix} \frac{P_{la}-P_{lv}}{c_{lv}(t)R_{mi}} & -\frac{P_{lv}-P_{sa}}{c_{lv}(t)R_{ao}} \\ -\frac{P_{la}-P_{lv}}{c_{la}(t)R_{mi}} & 0 \\ 0 & \frac{P_{lv}-P_{sa}}{c_{sa}R_{ao}} \end{bmatrix} \begin{bmatrix} u_1 \\ u_2 \end{bmatrix} \rightarrow$$

where $P_{lv}$, $P_{la}$ and $P_{sa}$ are left ventricular pressure (PLV), left atrial pressure (PLA) and aortic pressure respectively. The left ventricle (lv) and the left atrium (la) compliances are modeled as:

$$c_{lv}(t) = \begin{cases} c_{lv,s} \frac{1-\exp\left(-\frac{t}{\tau_s}\right)}{1-\exp\left(-\frac{T_s}{\tau_s}\right)}, & \text{for } 0 \leq t \leq T_s \\ c_{lv,d} \frac{1-\exp\left(-\frac{t-T_s}{\tau_d}\right)}{1-\exp\left(-\frac{T-T_s}{\tau_d}\right)}, & \text{for } T_s \leq t \leq T \end{cases} \quad (2)$$

$$c_{la}(t) = \begin{cases} c_{la,s} \frac{1-\exp\left(-\frac{t+\tau}{\tau_s}\right)}{1-\exp\left(-\frac{T_s}{\tau_s}\right)}, & \text{for } 0 \leq t \leq T_s \\ c_{la,d} \frac{1-\exp\left(-\frac{(t+\tau)-T_s}{\tau_d}\right)}{1-\exp\left(-\frac{T-T_s}{\tau_d}\right)}, & \text{for } T_s \leq t \leq T \end{cases} \rightarrow$$

where T is the duration of a cardiac cycle having a systolic duration of $T_s$, such that $T=1/HR$, where HR represents heart rate. $\tau_s$ and $\tau_d$ are the systolic and diastolic time constant respectively while $T-T_s$ represents a diastolic time duration. The constants $c_{lv,d}, c_{la,s}$ are the end systolic compliances and $c_{lv,d}, c_{la,d}$ represent the end diastolic compliances for the lv and the la respectively. $R_s$ and $c_{sa}$ represent the systemic vascular resistance and systemic vascular compliance, $R_{mi}$ and $R_{ao}$ are the mitral and aortic valve resistance. $u_1$ and $u_2$ represent control inputs for opening and closing a mitral valve and an aortic valve respectively, such that $$u_1 = \begin{cases} 0, & \text{if } P_{la} < P_{lv} \\ 1, & \text{otherwise} \end{cases}; u_2 = \begin{cases} 0, & \text{if } P_{lv} < P_{sa} \\ 1, & \text{otherwise} \end{cases} \rightarrow \quad (3)$$

It may be observed from the equation (2) that the hemodynamic CVS model is autonomous in nature due to the cyclic characteristics of the compliance functions. Within each cardiac cycle T, four different phases of operation in the left-ventricle may be observed (based on the control inputs $u_1$ and $u_2$) which are summarized in Table I below.

TABLE I

LV phases in a cardiac cycle

| Control Input | | Valve | | |
|---|---|---|---|---|
| $u_1$ | $u_2$ | Mitral | Aortic | LV Phase |
| 0 | 0 | Close | LV phase | Isovolumic relaxation |
| 1 | 0 | Open | Close | Ventricular filing |
| 0 | 0 | Close | Close | Isovolumic contraction |
| 0 | 1 | Close | Open | Ventricular ejection |

Hence each phase is illustrated by a differential equation from equation (1).

Additionally, the lv pressure (PLV) and lv volume (VLV) generate a loop (PV-loop) in each cardiac cycle based on the four phases shown in Table I above. The VLV is analytically defined as:

$$V_{lv} = c_{lv}(t)\dot{P}_{lv} + \dot{c}_{lv}(t)P_{lv} \quad (4)$$

Baroreflex auto-regulation is a homeostatic mechanism that helps to maintain the aortic pressure at nearly desired levels (for instance, 120/80 mmHg) by tuning the heart rate (HR), the left ventricle (lv) and the left atrium (la) compliances $c_{lv}(t), c_{la}(t)$ and the systemic vascular resistance. Baroreflex may be referred as without (W/O) control in the description and illustrations hereinafter. The auto-regulation starts with sensing of the aortic pressure by baroreceptor sensors, located at the carotid sinus to convert into afferent neural firing frequency. This frequency is further transformed into sympathetic and vagal neural frequencies by an efferent pathway. Based on this transformation, the regulation effector finally changes the HR, the $c_{lv}(t)$, the $c_{la}(t)$ and the systemic-vascular-resistance respectively in less than the duration of the cardiac cycle.

The Mitral valve is the gateway between the left ventricle (lv) and the left atrium (la). It only allows a unidirectional flow of blood from the left atrium (la) to fill the left ventricle (lv) during the ventricular filling phase. In Mitral stenosis (MS), the orifice of the valve's area gets narrower. Consequently, a high resistance across the stenotic valve causes blood to stay inside the left atrium (la), thus raising the la-pressure. Hence, the left atrium volume enlarges (hypertrophy) over time because it is required to produce higher pressure when it contracts against the high resistance stenotic valve. The reduced filling in the left ventricle decreases the ventricular stroke volume (SV), thus the cardiac output (CO) is reduced which subsequently reduces the aortic pressure, in spite of the proper functioning of the baroreflex auto-regulation mechanism.

A healthy mitral valve has an effective area of 4 to 6 cm². During MS this area gets decreased. Based on reduced valvular area (Normal area being>4 cm²), mild, moderate and severe MS have been graded as shown in Table II below. However, pathological symptoms are usually observed once the stenosis is in the moderate or severe range.

TABLE II

Severity of MS based on valvular area

| | Mild MS | Moderate MS | Severe MS |
|---|---|---|---|
| Valvular area (cm$^2$) | 2.5-4 | 1-2.5 | <1 |
| % reduction of valvular area compared to normal | <62.5% | 62.5%-80% | >80% |

During MS, the blood flow through the mitral valve is reduced because of the increasing valvular resistance. In accordance with the present disclosure, similar scenarios are simulated in the hemodynamic CVS model by increasing the parameter $R_{mi}$ of equation (1) as presented in Table III below.

TABLE III

Simulation of MS severity based on $R_{mi}$

| | Mild MS | Moderate MS | Severe MS |
|---|---|---|---|
| $R_{mi}$ (mm Hg · min/Lt) | 0.05 | 0.2 | 0.5 |
| % of simulated stenosis | 65% | 76% | 88% |

Figure 2:
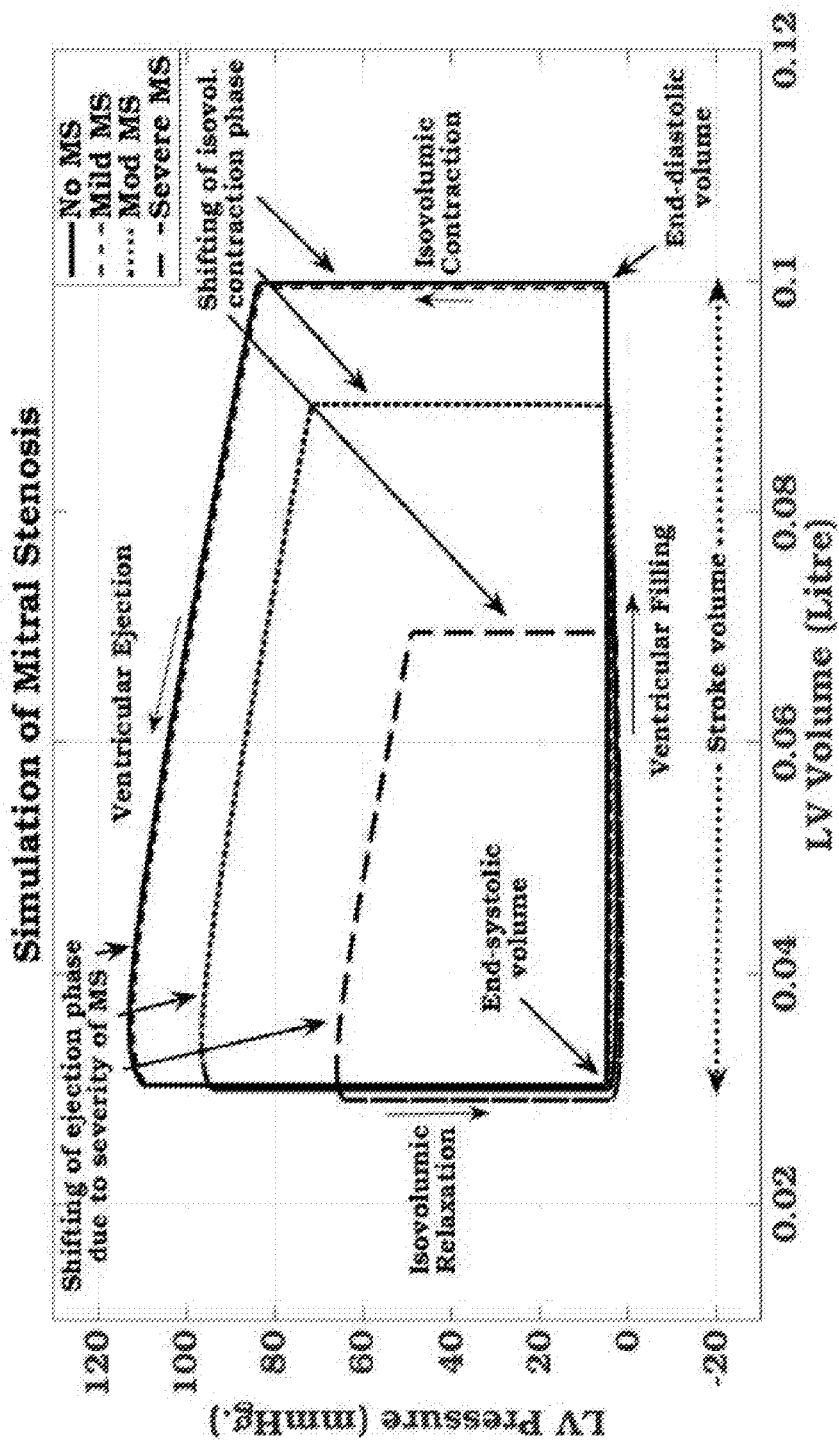
FIG. 2 illustrates a simulation of MS severity based on Mitral valve resistance $R_{mi}$, as known in the art.
Figure 3:
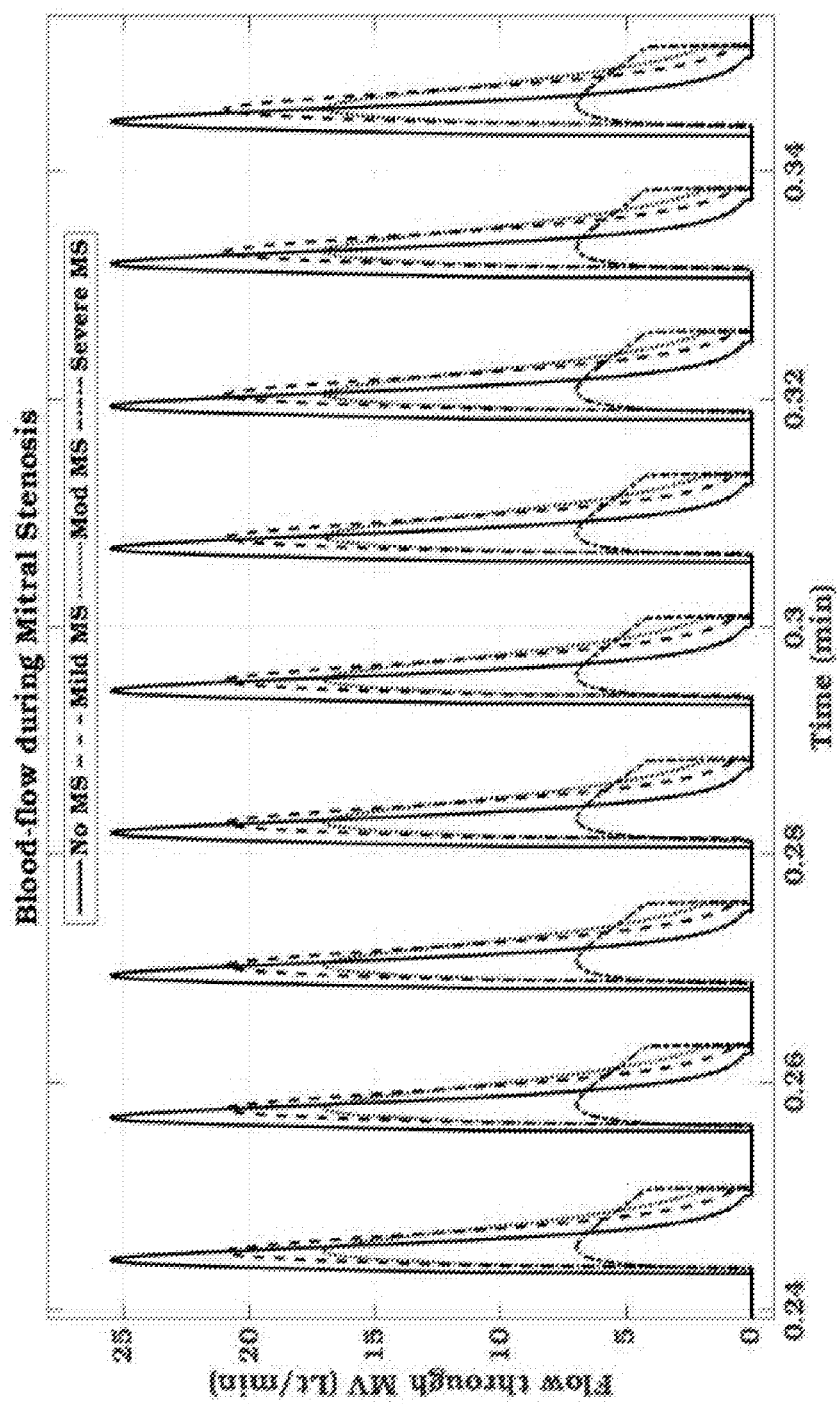
FIG. 3 illustrates blood flow through a Mitral valve during MS, as known in the art.

Based on the reduced valvular area, the ventricular filling phase is affected which subsequently shifts the isovolumetric contraction and ventricular ejection phases by reducing the lv-pressure (LVP) and lv-end-diastolic volume (LVEDV). The simulated MS of the present disclosure also exhibits similar consequences as shown in FIG. 2, wherein a simulation of MS severity based on Mitral valve resistance $R_{mi}$ is illustrated. Based on the disease severity, physiological hemodynamic parameters such as stroke volume (SV), cardiac output (CO), ejection fraction (EF) end diastolic volume (EDV), and the like are affected due to the reduced blood flow through the valve. FIG. 3 illustrates blood flow through the Mitral valve during MS, as known in the art. Such hemodynamic parameters may also be estimated from the PV-loop as shown in FIG. 2.

With the growing severity of MS, a patient may have heart failure because of the reduced CO. For a subject with mild MS, CO is still preserved by the auto-regulation mechanism. However, disease progression rate is usually around 0.1-0.3 cm$^2$/year and hence, the prevalence of moderate and severe MS cases is high. The present disclosure provides the system 100 that serves as the adaptive controller and simulates the effect in hemodynamic parameters to maintain a desired CO, corresponding to the healthy cardiovascular system, in patients having moderate to severe MS.

Figure 4:
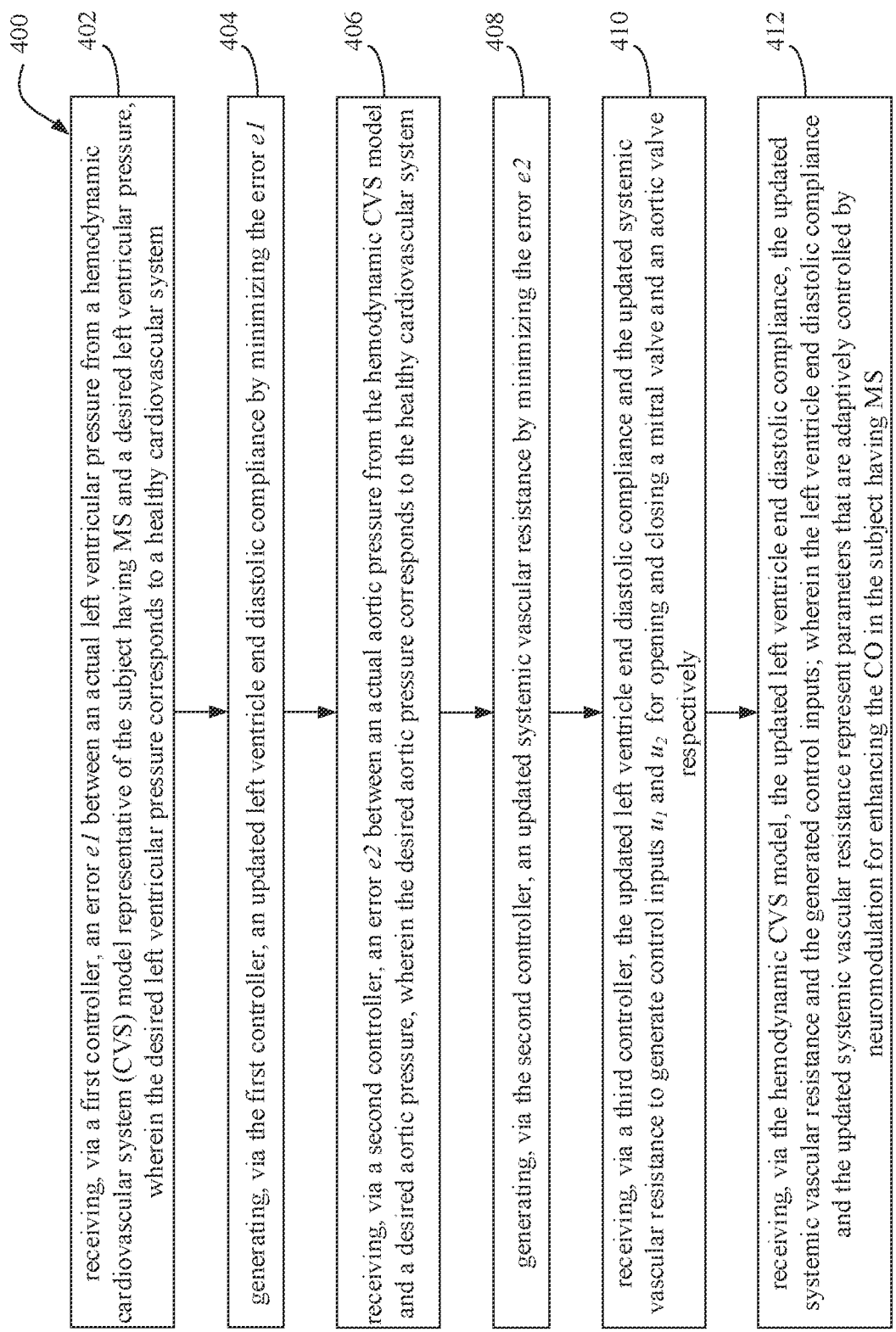
FIG. 4 illustrates an exemplary flow diagram of a computer implemented method for enhancing cardiac output (CO) in a subject having MS, in accordance with some embodiments of the present disclosure.
Figure 5:
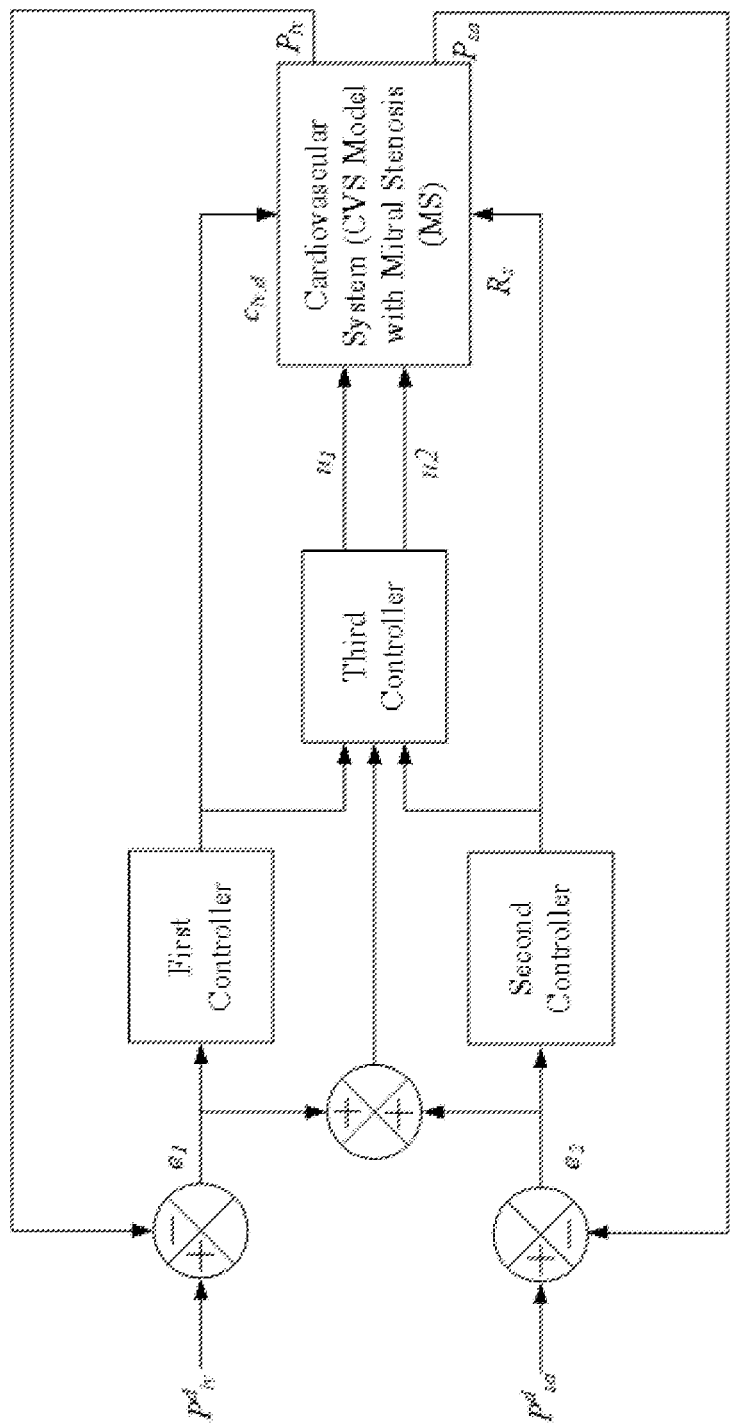
FIG. 5 illustrates a block diagram representation of the adaptive control of the method of FIG. 4, in accordance with some embodiments of the present disclosure.

FIG. 4 illustrates an exemplary flow diagram for a computer implemented method 400 for enhancing cardiac output (CO) in a subject having MS, in accordance with an embodiment of the present disclosure. FIG. 5 illustrates a block diagram representation of the adaptive control of the method of FIG. 4, in accordance with some embodiments of the present disclosure. In an embodiment, the system 100 includes one or more data storage devices or memory 102 operatively coupled to the one or more processors 104 and is configured to store instructions configured for execution of steps of the method 400 by the one or more processors 104. The steps of the method 400 will now be explained in detail with reference to the components of the system 100 of FIG. 1 and the block diagram of FIG. 5. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In an embodiment, the adaptive controller illustrated as system 100 comprises the hemodynamic CVS model representative of the subject having MS along with a plurality of controllers, referred generally as a first controller, a second controller and a third controller for ease of explanation. The main purpose of the adaptive controller is to maintain the cardiac output (CO) at the physiological healthy limits for a cardiac condition with moderate or severe MS. To realize this, the stroke volume (SV) demands to be recovered as CO=SV×HR, wherein HR is a constant. Subsequently, the end-diastolic volume (EDV) requires to be updated as SV=EDV−ESV, where ESV represents the end-systolic volume which is fixed for any type of MS. In order to increase EDV, the method 400 of the present disclosure artificially enhances the lv end-diastolic-compliance $c_{lv,d}$ and the systemic-vascular-resistance $R_s$ such that the blood flow through the diseased valve can be regulated using the parameter $u_1$. At the same time, the flow through the aortic valve is guided by the parameter $u_1$ to accomplish the desired aortic pressure. The control mechanism enhances the blood flow through the left ventricle during the various MS condition through a cascaded control as illustrated in FIG. 5.

The first controller and the second controller are employed to estimate cardiac parameters that manage cardiac auto-regulation such as the left ventricle end diastolic compliance and the systemic vascular resistance respectively, using the hemodynamic CVS model representative of the subject having MS. Accordingly, in an embodiment of the present disclosure, the one or more processors 104 serving as the first controller (left ventricle end diastolic controller) are configured to receive, at step 402, an error e1 between an actual left ventricular pressure $P_{lv}$ from the hemodynamic CVS model representative of the subject having MS and a desired left ventricular pressure $P_{lv}^d$, wherein the desired left ventricular pressure (varies between subjects and depends on healthy data obtained for the subject) corresponds to a healthy cardiovascular system. The first controller is further configured to generate an updated left ventricle end diastolic compliance $\tilde{c}_{lv,d}$, at step 404, by minimizing the error e1. The error is minimized by tuning the gain of the first controller. In accordance with an embodiment of the present disclosure, the one or more processors 104 serving as the second controller (systemic-vascular-resistance controller) are configured to receive, at step 406, an error e2 between an actual aortic pressure $P_{sa}$ from the hemodynamic CVS model and a desired aortic pressure $p_{sa}^d$, wherein the desired aortic pressure (for instance, 120/80 mmHg) corresponds to the healthy cardiovascular system. The second controller is further configured to generate an updated systemic vascular resistance $\tilde{R}_s$, at step 408, by minimizing the error e2. The error is minimized by tuning the gain of the second controller.

As per medical reports provided by LiDCO entitled "*Normal Hemodynamic Parameters*", there exists a physiological acceptable range for the lv end diastolic compliance and the systemic vascular resistance. In accordance with the present disclosure, the ranges are assumed to be [$c_{lv,d}^{min}$, $c_{lv,d}^{max}$] and [$R_s^{min}$, $R_s^{max}$] respectively.

Estimating the lv end diastolic compliance by the first controller. Considering the lv compliance function of equation (2) for the diastolic phase, $$c_{lv}(t) = c_{lv,d} \frac{1-\exp\left(-\frac{t-T_s}{\tau_d}\right)}{1-\exp\left(-\frac{T-T_s}{\tau_d}\right)} \text{ for } T_s \leq t \leq T$$

Linearizing the exponential term and differentiating the above equation with respect to time, $$\frac{\dot{c}_{lv}(t)}{c_{lv}(t)} = \frac{\ln(c_{lv,d})}{T-T_s} \rightarrow \quad (5)$$

The error e1 is considered to approximate the lv end diastolic compliance.

$$e1 = P_{lv} - P_{lv}^d \quad (6)$$

Differentiating equation (6) and inserting the result as obtained from equation (1) and equation (5), $$\dot{e}1 = \frac{\ln(c_{lv,d})}{T-T_s} P_{lv} - \dot{P}_{lv}^d$$

In order to minimize the error, $\dot{e}1 \approx 0$.

In accordance with an embodiment of the present disclosure, the updated left ventricle end diastolic compliance $\tilde{c}_{lv,d}$ is based on the actual left ventricular pressure $P_{lv}$, a rate of change of the desired left ventricular pressure $\dot{P}_{lv}^d$ and a diastolic time duration $T-T_s$, wherein T represents duration of a cardiac cycle having a systolic duration $T_s$, such that the $\tilde{c}_{lv,d}$ is limited to a physiological acceptable range for left ventricle end diastolic compliance $[c_{lv,d}^{min}, c_{lv,d}^{max}]$. Accordingly, the lv end diastolic compliance is first estimated as $$= \hat{c}_{lv,d} = \exp\left(-\frac{\dot{P}_{lv}^d(T-T_s)}{P_{lv}}\right) \rightarrow \quad (7)$$

Using the physiological acceptable range for the lv end diastolic compliance, the updated left ventricle end diastolic compliance $\tilde{c}_{lv,d}$ is represented according to the equation $$\tilde{c}_{lv,d} = \begin{cases} c_{lv,d}^{max} \text{ if } \hat{c}_{lv,d} > c_{lv,d}^{max} \\ \hat{c}_{lv,d} \text{ if } c_{lv,d}^{max} \geq \hat{c}_{lv,d} \geq c_{lv,d}^{min} \rightarrow \\ c_{lv,d}^{min} \text{ if } \hat{c}_{lv,d} < c_{lv,d}^{min} \end{cases} \quad (8)$$

Estimating the systemic vascular resistance by the second controller:

The error e2 is considered to approximate the systemic vascular resistance.

$$e2 = P_{sa} - P_{sa}^d \quad (9)$$

Differentiating the equation (9) and inserting the value as obtained from equation (1), $$\dot{e}2 = \frac{1}{c_{sa}R_s}(P_{sa} - P_{la}) - \dot{P}_{sa}^d \rightarrow \quad (10)$$

In accordance with the present disclosure, the updated systemic vascular resistance $\tilde{R}_s$ is based on the actual aortic pressure $P_{sa}$, a rate of change of the desired aortic pressure $\dot{P}_{sa}^d$ and a left atrial pressure $P_{la}$, such that the $\tilde{R}_s$ is limited to a physiological acceptable range for systemic vascular resistance $[R_s^{min}, R_s^{max}]$. Accordingly, $\hat{R}_s$ is first estimated as $$\hat{R}_s = -\frac{P_{sa} - P_{la}}{c_{sa}\dot{P}_{sa}^d} \rightarrow \quad (11)$$

Using the physiological acceptable range for the systemic vascular resistance, the updated systemic vascular resistance $\tilde{R}_s$ is represented according to the equation $$\begin{cases} R_s^{max} \text{ if } \hat{R}_s > R_s^{max} \\ \hat{R}_s \text{ if } R_s^{max} \geq \hat{R}_s \geq R_s^{min}, \rightarrow \\ R_s^{min} \text{ if } \hat{R}_s < R_s^{min} \end{cases} \quad (12)$$

Once the parameters that are to be adaptively controlled are estimated, the control inputs $u_1$ and $u_2$ need to be re-estimated to manage the blood flow through the mitral valve and the aortic valve respectively. The third controller is employed to manage blood flow through the diseased valve by exploiting the outcomes from the first controller and the second controller. Accordingly, in an embodiment of the present disclosure, the one or more processors 104 serving as the third controller, are configured to receive, at step 410, the updated left ventricle end diastolic compliance $\tilde{c}_{lv,d}$ and the updated systemic vascular resistance $\tilde{R}_s$ to generate control inputs $u_1$ and $u_2$ for opening and closing the mitral valve and the aortic valve respectively.

In a state space form, the equation (1) may be written as $$\dot{x} = A(t)x + G(x,t)u \quad (13)$$

where $x = [P_{lv}\ P_{la}\ P_{sa}]^T$, $P_{la}$ representing a left atrial pressure, $u = [u_1\ u_2]^T$, A(t) is a state matrix in the equation (1) and is represented as $$\begin{bmatrix} -\frac{\dot{c}_{lv}(t)}{c_{lv}(t)} & 0 & 0 \\ 0 & -\frac{\dot{c}_{la}(t)}{c_{la}(t)} & \frac{1}{c_{la}(t)R_s} \\ 0 & \frac{1}{c_{sa}R_s} & -\frac{1}{c_{sa}R_s} \end{bmatrix},$$

G(x,t) is an input matrix in the equation (1) and is represented as $$\begin{bmatrix} \frac{P_{la}-P_{lv}}{c_{lv}(t)R_{mi}} & -\frac{P_{lv}-P_{sa}}{c_{lv}(t)R_{ao}} \\ -\frac{P_{la}-P_{lv}}{c_{la}(t)R_{mi}} & 0 \\ 0 & \frac{P_{lv}-P_{sa}}{c_{sa}R_{ao}} \end{bmatrix},$$

$x^d(t) = [P_{lv}\ P_{la}^d\ P_{sa}^d]^T$ represents a desired state corresponding to the healthy cardiovascular system, $$\tilde{A}(t) = A(t)|_{\tilde{R}_s, \tilde{c}_{lv,d}}, \text{ and } \tilde{G}(x,t) = G(x,t)|_{\tilde{c}_{lv,d}}.$$

In accordance with the present disclosure, a cascaded control unit u based on the control inputs $u_1$ and $u_2$ is provided to the hemodynamic CVS model, wherein the cascaded control unit u is represented in a state space form according to the equation, $$\tilde{u} = \tilde{G}^{-1}(\dot{x}^d - \tilde{A}x)|_{\tilde{R}_s = \tilde{R}_s, c_{lv,d} = \tilde{c}_{lv,d}} \rightarrow \quad (14)$$

In accordance with an embodiment of the present disclosure, the one or more processors 104 serving as the hemodynamic CVS model, are configured to receive, at step 412, the updated left ventricle end diastolic compliance $\tilde{c}_{lv,d}$ the updated systemic vascular resistance $R_s$ and the generated control inputs $u_1$ and $u_2$ (412); wherein the $\tilde{c}_{lv,d}$ (contractility) and the $\tilde{R}_s$ (vagal tone) represent parameters that are adaptively controlled by neuromodulation for enhancing the CO in the subject having MS by enhancing the end diastolic volume EDV which in turn enhances the CO.

Stability Analysis: To analyze the stability of the adaptive controller or the system 100 of the present disclosure, an error function $e=\tilde{x}-x$ is assumed. The time derivative of e is written as $$\dot{e} = \dot{\tilde{x}} - \dot{x} \quad (15)$$
$$= [\tilde{A}(t) - A(t)]x + [\tilde{G}(x,t) - G(x,t)]u$$

Considering $v=\frac{1}{2}e^2$ as the Lyapunov candidate (Refer A Codrean et al. in *Delay effect on cardiovascular regulation—a systems analysis approach*), the time derivative of v based on equation (15) is represented as $$\dot{v}=e[[\tilde{A}(t)-A(t)]x+[\tilde{G}(x,t)-G(x,t)]u] \quad (16)$$

In order to asymptotically stabilize the control laws, $\dot{v}$ should be negative definite, i.e. $\dot{v}<0$. Hence the right hand side of Equation 16 needs to be less than zero.

The terms $[\tilde{A}(t)-A(t)]$ and $[\tilde{G}(x,t)-G(x,t)]$ can be expanded from equations (1) and equation (5) as $$[\tilde{A}(t) - A(t)] = \begin{bmatrix} \ln\frac{c_{lv,d}}{\tilde{c}_{lv,d}} & 0 & 0 \\ \frac{T-T_s}{T-T_s} & 0 & \frac{1}{c_{la}(t)}\left[\frac{1}{\tilde{R}_s} - \frac{1}{R_s}\right] \\ 0 & \frac{1}{c_{sa}}\left[\frac{1}{\tilde{R}_s} - \frac{1}{R_s}\right] & -\frac{1}{c_{sa}}\left[\frac{1}{\tilde{R}_s} - \frac{1}{R_s}\right] \end{bmatrix} \quad (17)$$

$$[\tilde{G}(x,t) - G(x,t)] = \begin{bmatrix} q_{mi}\left[\frac{1}{\tilde{c}_{lv}(t)} - \frac{1}{c_{lv}(t)}\right] & q_{ao}\left[\frac{1}{\tilde{c}_{lv}(t)} - \frac{1}{c_{lv}(t)}\right] \\ q_{mi}\left[\frac{1}{\tilde{c}_{lv}(t)} - \frac{1}{c_{lv}(t)}\right] & 0 \\ 0 & 0 \end{bmatrix}$$

where $$q_{mi} = \frac{P_{la} - P_{lv}}{R_{mi}}, \quad q_{ao} = (P_{lv} - P_{sa})/R_{ao}.$$

For MS, as per the control requirements, $\tilde{c}_{lv,d} \geq c_{lv,d}$, $\tilde{R}_s \geq R_s$ and $\tilde{c}_{lv,d}(t) \geq c_{lv}(t)$, which results in $[\tilde{A}(t)-A(t)] \leq 0$ and $[\tilde{G}(x,t)-G(x,t)] \leq 0$ and hence $\dot{v}<0$. Therefore, the equation (17) is negative definite for the control requirements of the present disclosure and subsequently stabilizes the control actions in the sense of the Lyapunov candidate.

Simulation Results

The simulations were executed on a system having 16 GB of RAM with Intel® core-i7 processor in MATLAB™/Simulink software environment. The parametric values as shown in Table IV below were used for the simulation study.

TABLE IV

| Model parameters | | |
|---|---|---|
| Parameters | Value | Physiological meaning |
| Resistances (mmHg · min/Lt.) | | |
| $R_s$ | 17.86 | Systemic vascular resistance |
| $R_{ao}$ | 0.01 | Aortic valve resistance |
| Compliances (Lt/mmHg.) | | |
| $c_{sa}$ | 0.0018 | Systemic compliance |
| $c_{lv,s}$ | 3e−05 | LV end systolic compliance |
| $c_{lv,d}$ | 0.0146 | LV end diastolic compliance |
| $c_{la,s}$ | 3e−05 | LA end systolic compliance |
| $c_{la,d}$ | 0.013 | LA end diastolic compliance |
| Timing parameters (min.) | | |
| HR | 80 | Heart rate |
| $T_s$ | 0.005 | Systolic duration |
| $\tau_s$ | 0.0025 | Systolic time constant |
| $\tau_d$ | 1e−03 | Diastolic time constant |
| $\tau$ | 0.006 | Delay between la and lv |

Based on the severity level of MS (Table II), the percentage of reduction of the valve area was measured as compared to the normal. Also, by varying the valve resistance $R_{mi}$ (Table III), the blood flow through the mitral valve was determined (as shown in FIG. 3). Based on these outcomes, the percentage of simulated stenosis in the CVS model of the present disclosure was estimated. The result is presented in Table III above.

Analysis of the PV-loop in MS condition: The MS may be accurately examined by the PV-loops using hemodynamic parameters such as CO, SV, EDV, and the like. A result of such an examination in FIG. 6A through FIG. 6C, wherein a comparative analysis of the MS severity—Mild MS, Moderate MS and Severe MS respectively, with respect to the Left ventricle Pressure Left ventricle Volume loop (PV-loop), in accordance with some embodiments of the present disclosure is illustrated. The PV-loop without (W/O) control is referred from "A physiological control strategy for continuous flow left ventricular assist devices: The power ratio controller" by F. Schrodel et al. Also Table V below provides a comparative analysis of the hemodynamic parameters with respect to the medical reports provided by LidCO in "Normal Hemodynamic Parameters".

TABLE V

| Comparative analysis of the hemodynamic parameters | | | | | | | | | | | | |
|---|---|---|---|---|---|---|---|---|---|---|---|---|
| | SV (Lt/beat) | | | CO (Lt/min) | | | EDV (Lt.) | | | MAP (mmHg.) | | |
| Types of MS | Req. | BR | Disc. | Req. | BR | Disc. | Req. | BR | Disc. | Req. | BR | Disc. |
| Mild MS | 0.05-1 | 0.07 | 0.07 | 4-8 | 5.6 | 5.6 | 0.09-0.15 | 0.1 | 0.1 | 70-105 | 96 | 97 |
| Mod. MS | 0.05-1 | 0.059 | 0.06 | 4-8 | 4.72 | 4.8 | 0.09-0.15 | 0.89 | 0.09 | 70-105 | 83 | 100 |

TABLE V-continued

Comparative analysis of the hemodynamic parameters

| Types of MS | SV (Lt/beat) | | | CO (Lt/min) | | | EDV (Lt.) | | | MAP (mmHg.) | | |
|---|---|---|---|---|---|---|---|---|---|---|---|---|
| | Req. | BR | Disc. | Req. | BR | Disc. | Req. | BR | Disc. | Req. | BR | Disc. |
| Sev. MS | 0.05-1 | 0.04 | 0.055 | 4-8 | 3.2 | 4.4 | 0.09-0.15 | 0.069 | 0.085 | 70-105 | 55 | 104 |

Mod. = Moderate, Sev. = Severe, Req. = Required, BR = Baroreflex Disc. = Present disclosure, SV = Stroke volume, CO = Cardiac output, EDV = End diastolic volume, MAP = Mean arterial pressure.

Figure 6A:
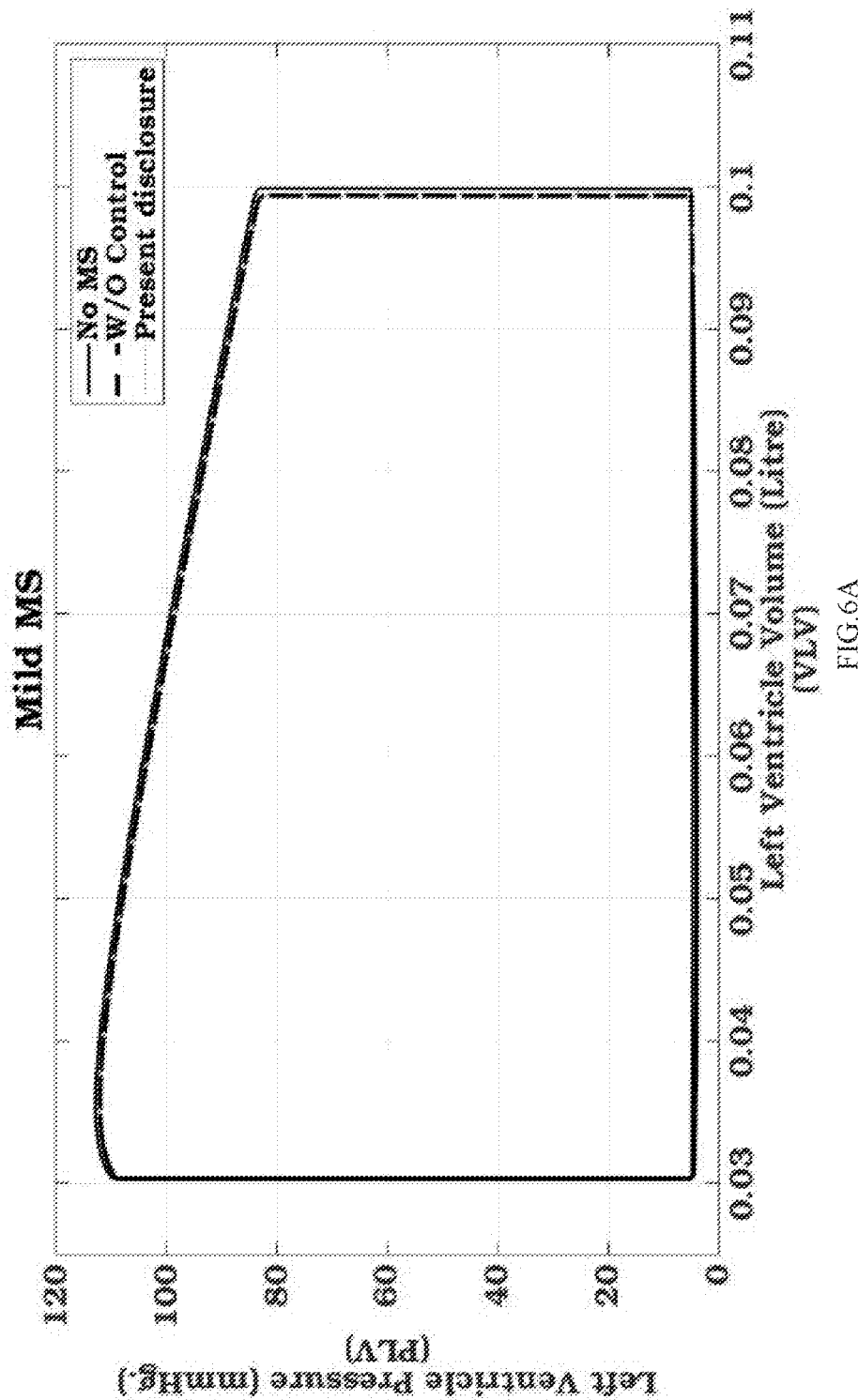
Figure 6C:
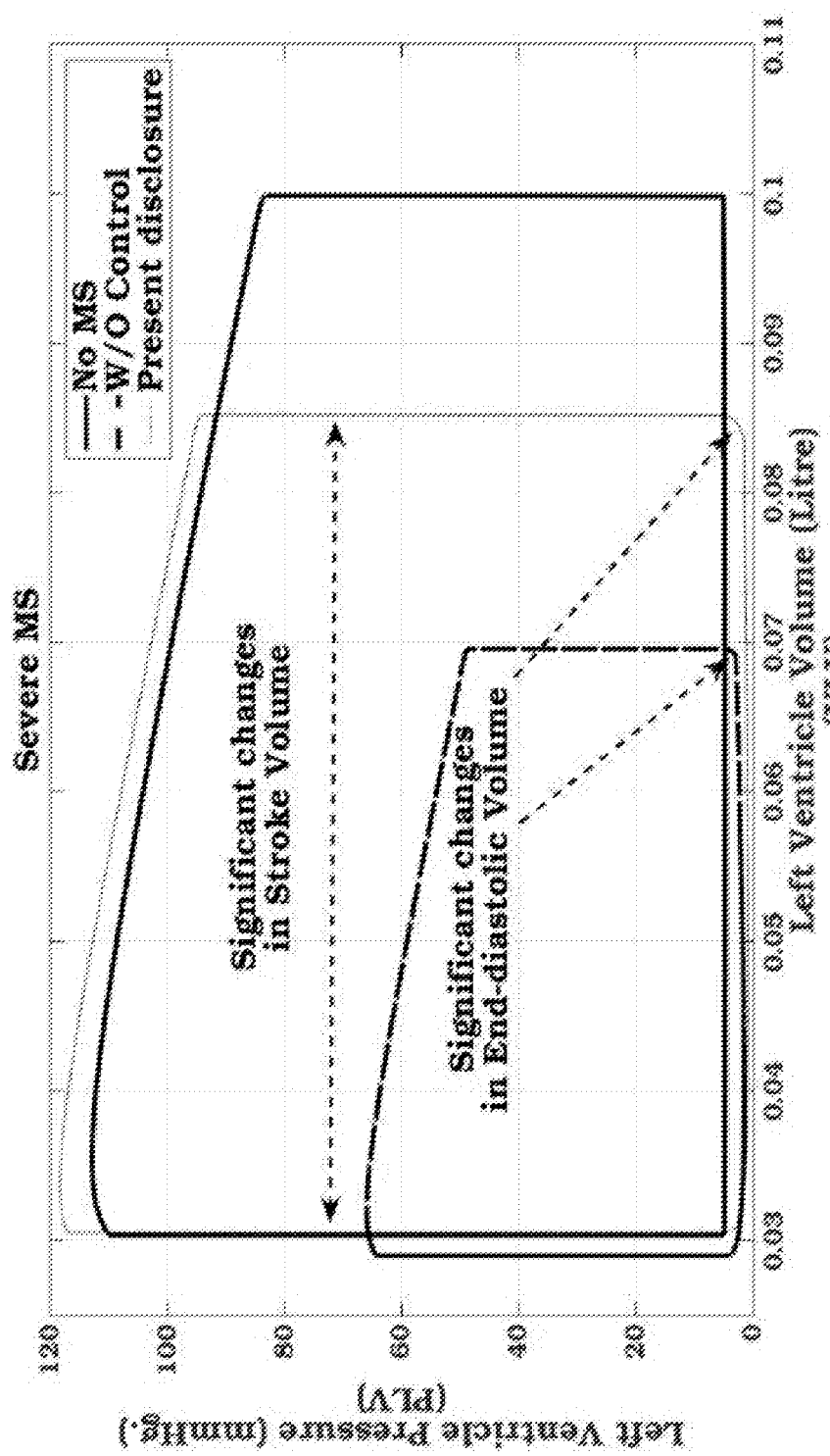

For mild MS (as shown in FIG. 6A), both the loops, i.e. baroreflex and the loop obtained by the system and method of the present disclosure, coincide with the desired one. Hence, the hemodynamic parameters such as CO, SV, and EDV are identical and within the required range (Refer Table V). With an increase in severity, a small variation between the loops has been witnessed (FIG. 6B), however, the isovolumetric contraction phases for both techniques are shifted towards left from the desired outcome. Hence, CO, SV, and EDV are degraded but within the required range. This outcome may affect the metabolic rate of the body as CO is reduced. With the further increment of $R_{mi}$, the disease progresses towards the severity level. In this situation, the baroreflex technique completely fails to maintain the required physiological ranges that are strictly required for a patient to survive (FIG. 6C).

However, with the system and method of the present disclosure, although the isovolumetric contraction phase has been shifted towards left from the required, the hemodynamic parameters are within the required range (Refer Table V). From this analysis, it can be concluded that the system and method of the present disclosure is capable of bringing down hemodynamic parameters to a normal operating range.

Figure 7:
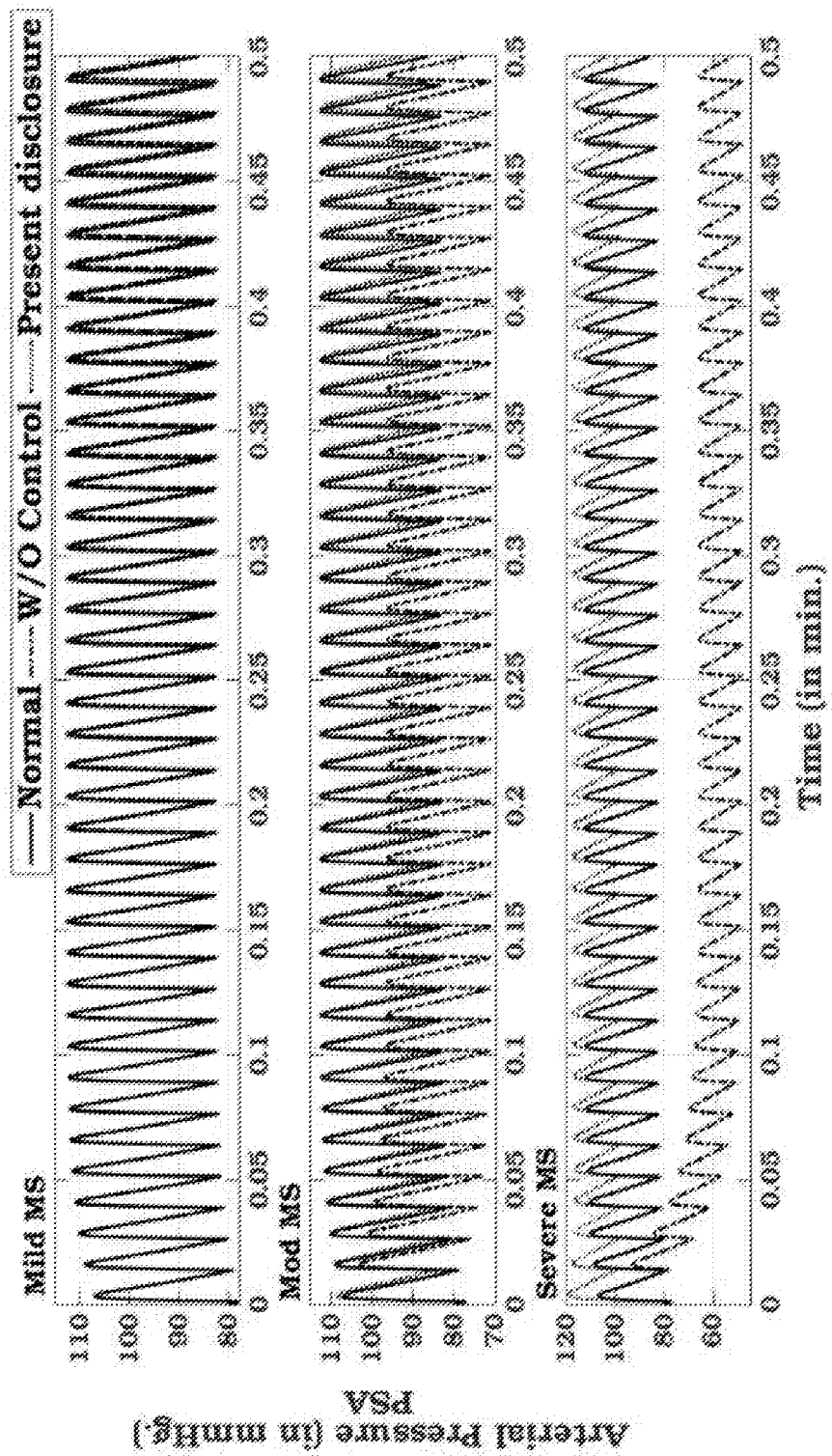
FIG. 7 illustrates variations of Aortic Pressure with MS severity, in accordance with some embodiments of the present disclosure.

Analysis of aortic pressure during MS: During moderate/severe MS, the blood flow through the mitral valve is significantly decreased, which consequently reduces the aortic flow. Hence, the aortic pressure $P_{sa}$ drops than the required level. As a result, the body's essential metabolism rate is greatly impacted and may damage the organs and tissues. The result of the investigation on the aortic pressure $P_{sa}$ is shown in FIG. 7, wherein variations of Aortic Pressure with MS severity, in accordance with some embodiments of the present disclosure are shown. For mild MS, no variation in $P_{sa}$ has been perceived between the baroreflex (without controller) and the system and method of the present disclosure. However, with increasing severity, $P_{sa}$ is drastically reduced in the baroreflex auto-regulation technique, hence the required mean-arterial-pressure (MAP) is not maintained. However, the system and method of the present disclosure is able to sustain the desired MAP level by optimally tuning the vascular resistance ($R_s$) (Refer Table V).

Figure 8:
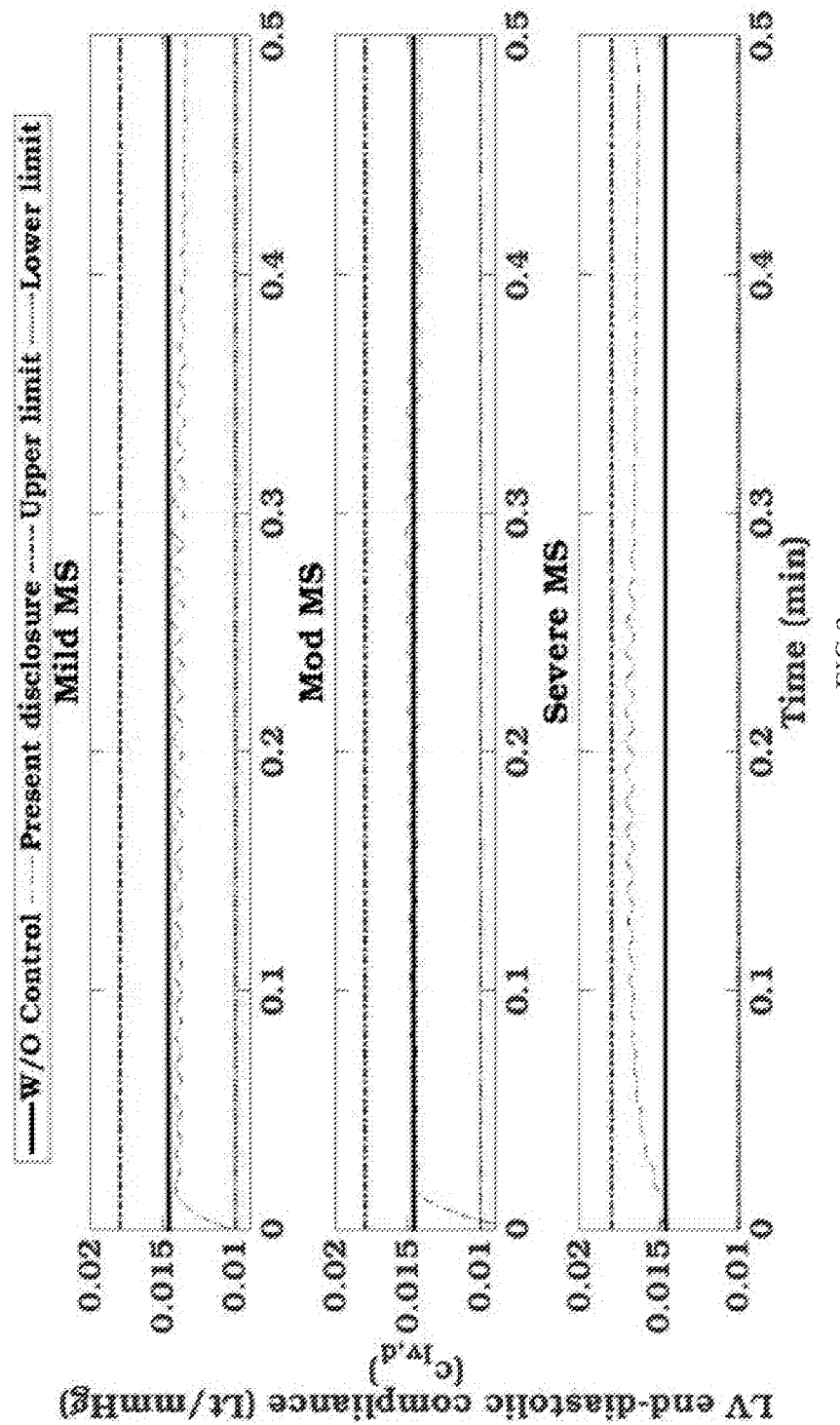
FIG. 8 illustrates evaluated left ventricle end diastolic compliances in accordance with some embodiments of the present disclosure with actual physiological ranges.
Figure 9:
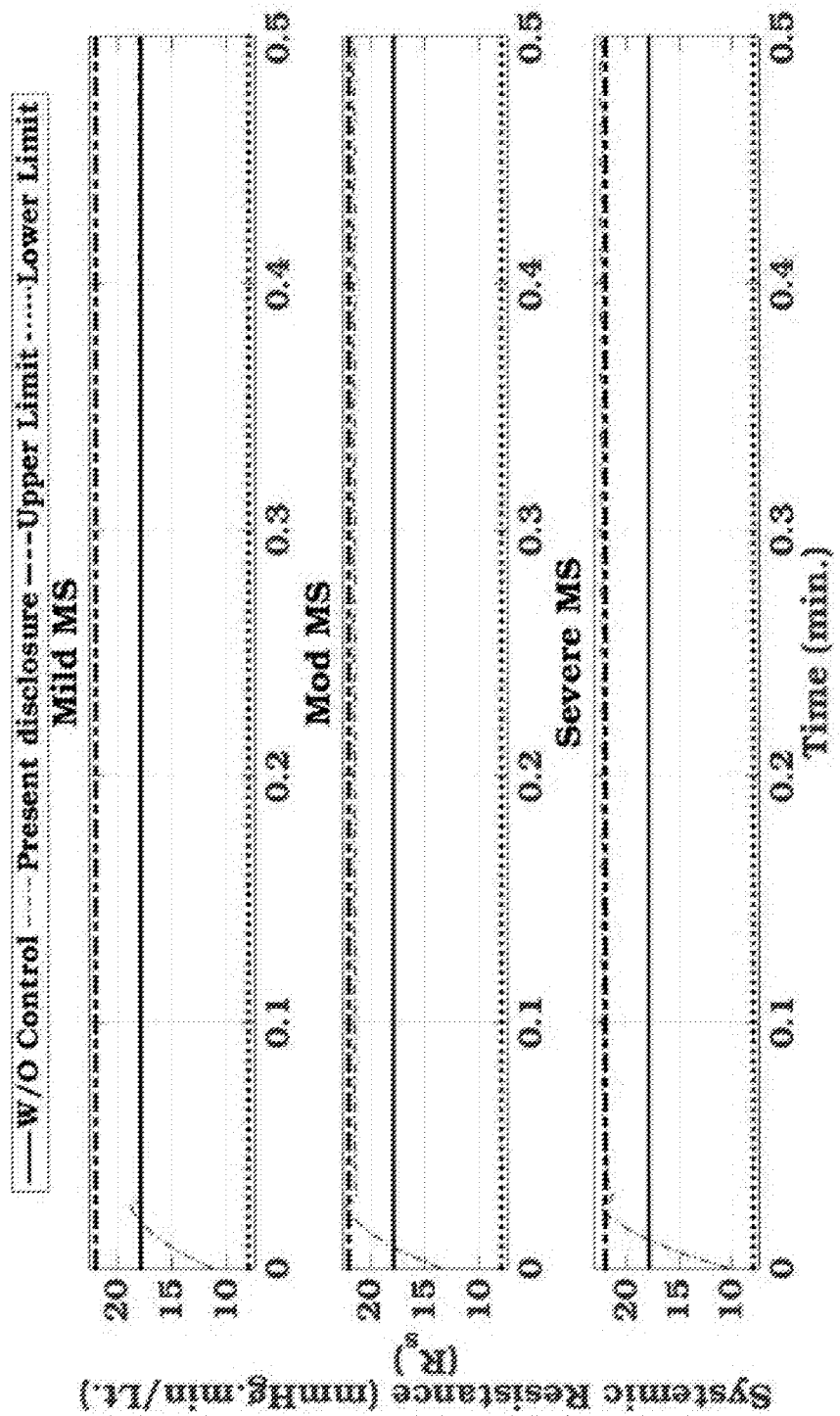
FIG. 9 illustrates evaluated systemic vascular resistance, in accordance with some embodiments of the present disclosure with actual physiological ranges.

Comparison of evaluated controlled parameters: The controlled parameters have been evaluated during the entire cardiac duration. FIG. 8 illustrates evaluated left ventricle end diastolic compliances in accordance with some embodiments of the present disclosure with actual physiological ranges. While comparing the lv-end-diastolic compliance ($c_{lv,d}$), it was observed that the evaluated parameter is approximately equal for both techniques in mild and moderate MS condition. Further increment on stenosis, ($c_{lv,d}$), is increased more as compared to the baroreflex which significantly enhances the end-diastolic volume (EDV). However, it is noted that the estimated control parameter is always within the actual physiological range as suggested by the medical reports of LiDCO in "Normal Hemodynamic Parameters". Hence, from this outcome, it may be concluded that such control variation is possible to achieve in real scenarios. Further a study of the variation of the systemic vascular resistance was evaluated. FIG. 9 illustrates evaluated systemic vascular resistance, in accordance with some embodiments of the present disclosure with actual physiological ranges. In order to reduce the $P_{sa}$ error, the $R_s$ has been reached to a theoretical maximum limit for the severe MS, thus it is the maximum range of the systemic vascular resistance with the system and method of the present disclosure.

Simulation results indicate that the system and method of the present disclosure have a significant effect in remodeling left ventricular dynamics and are capable of correcting hemodynamic conditions during mild to severe MS. The parameters controlled by neuromodulation include the lv end-diastolic compliance, the systemic vascular resistance and the heart rate. The heart rate being considered fixed, the method 400 using the adaptive controller referred as the system 100 of the present disclosure simulates the valvular disease conditions to modulate contractility $c_{lv,d}$ and vagal tone $R_s$ for adjusting hemodynamic imbalances during MS.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method (400) for enhancing cardiac output (CO) in a subject having Mitral Stenosis (MS), the method comprising the steps of:
   receiving, via one or more hardware processors serving as a first controller, an error e1 between an actual left ventricular pressure $P_{lv}$ obtained from an adaptive controller comprising a hemodynamic cardiovascular system (CVS) model representative of the subject having MS and a desired left ventricular pressure pa wherein the desired left ventricular pressure corresponds to a healthy cardiovascular system (402);
   generating an updated left ventricle end diastolic compliance $\tilde{c}_{lv,d}$ via the first controller, by minimizing the error e1 (404);
   receiving, via one or more hardware processors serving as a second controller, an error e2 between an actual aortic pressure $P_{sa}$ obtained from an adaptive controller comprising the hemodynamic CVS model and a desired aortic pressure $P_{sa}^{d}$, wherein the desired aortic pressure corresponds to the healthy cardiovascular system (406);
   generating an updated systemic vascular resistance $\tilde{R}_s$, via the second controller, by minimizing the error e2 (408);
   receiving, via one or more hardware processors serving as a third controller, the updated left ventricle end diastolic compliance $\tilde{c}_{lv,d}$ and the updated systemic vascular resistance $\tilde{R}_s$ to generate control inputs $u_1$ and $u_2$ for opening and closing a mitral valve and an aortic valve respectively (410) of the subject;
   receiving, via the adaptive controller comprising the hemodynamic CVS model, the updated left ventricle end diastolic compliance $\tilde{c}_{lv,d}$, the updated systemic vascular resistance $\tilde{R}_s$ and the generated control inputs $u_1$ and $u_2$ (412); and
   enhancing, via the one or more hardware processors serving as the first controller, the second controller and the third controller, the CO in the subject having MS by using the generated control inputs $u_1$ and $u_2$ and adaptively controlling via the hemodynamic CVS model, the parameters of updated left ventricle end diastolic compliance $\tilde{c}_{lv,d}$, and the updated systemic vascular resistance $\tilde{R}_s$ by neuromodulation.

2. The processor implemented method of claim 1, wherein the updated left ventricle end diastolic compliance $\tilde{c}_{lv,d}$ is based on the actual left ventricular pressure $P_{lv}$, a rate of change of the desired left ventricular pressure $\dot{P}_{lv}^{d}$ and a diastolic time duration $T-T_s$, and wherein T represents duration of a cardiac cycle having a systolic duration $T_s$, such that the $\tilde{c}_{lv,d}$ is limited to a physiological acceptable range for left ventricle end diastolic compliance $[c_{lv,d}^{min}, c_{lv,d}^{max}]$.

3. The processor implemented method of claim 2, wherein the updated left ventricle end diastolic compliance $\tilde{c}_{lv,d}$ is represented according to the equation $$\tilde{c}_{lv,d} = \begin{cases} c_{lv,d}^{max} & \text{if } \hat{c}_{lv,d} > c_{lv,d}^{max} \\ \hat{c}_{lv,d} & \text{if } c_{lv,d}^{max} \geq \hat{c}_{lv,d} \geq c_{lv,d}^{min} \\ c_{lv,d}^{min} & \text{if } \hat{c}_{lv,d} < c_{lv,d}^{min} \end{cases},$$

and wherein $\hat{c}_{lv,d}$ is an estimated left ventricle end diastolic compliance and is represented according to the equation $$\hat{c}_{lv,d} = \exp\left(-\frac{\dot{P}_{lv}^{d}(T-T_s)}{P_{lv}}\right).$$

4. The processor implemented method of claim 1, wherein the updated systemic vascular resistance $\tilde{R}_s$ is based on the actual aortic pressure $P_{sa}$, a rate of change of the desired aortic pressure $\dot{P}_{sa}^{d}$ and a left atrial pressure $P_{la}$, such that the $\tilde{R}_s$ is limited to a physiological acceptable range for systemic vascular resistance $[R_s^{min}, R_s^{max}]$.

5. The processor implemented method of claim 4, wherein the updated systemic vascular resistance $\tilde{R}_s$ is represented according to the equation $$\tilde{R}_s = \begin{cases} R_s^{max} & \text{if } \hat{R}_s > R_s^{max} \\ \hat{R}_s & \text{if } R_s^{max} \geq \hat{R}_s \geq R_s^{min} \\ R_s^{min} & \text{if } \hat{R}_s < R_s^{min} \end{cases},$$

wherein $\hat{R}_s$ is an estimated systemic vascular resistance and is represented according to the equation $$\hat{R}_s = -\frac{P_{sa} - P_{la}}{c_{sa}\dot{P}_{sa}^d},$$

and wherein $c_{sa}$ is a constant representing a systemic vascular compliance.

6. The processor implemented method of claim 1, wherein a cascaded control unit $\tilde{u}$ based on the control inputs $u_1$ and $u_2$ is provided to the hemodynamic CVS model, wherein the cascaded control unit it is represented in a state space form according to the equation $$\tilde{u} = \tilde{G}^{-1}(\dot{x}^d - \tilde{A}x)\big|_{R_s = \tilde{R}_s, c_{lv,d} = \tilde{c}_{lv,d}},$$

and wherein $\dot{x} = A(t)x + G(x,t)u$,
$x = [P_{lv}\ P_{la}\ P_{sa}]^T$, $P_{la}$ representing a left atrial pressure,
$u = [u_1\ u_2]^T$,
$A(t)$ is a state matrix represented as $$\begin{bmatrix} -\frac{\dot{c}_{lv}(t)}{c_{lv}(t)} & 0 & 0 \\ 0 & -\frac{\dot{c}_{la}(t)}{c_{la}(t)} & \frac{1}{c_{la}(t)R_s} \\ 0 & \frac{1}{c_{sa}R_s} & -\frac{1}{c_{sa}R_s} \end{bmatrix},$$

$G(x, t)$ is an input matrix represented as $$\begin{bmatrix} \frac{P_{la} - P_{lv}}{c_{lv}(t)R_{mi}} & -\frac{P_{lv} - P_{sa}}{c_{lv}(t)R_{ao}} \\ -\frac{P_{la} - P_{lv}}{c_{la}(t)R_{mi}} & 0 \\ 0 & \frac{P_{lv} - P_{sa}}{c_{sa}R_{ao}} \end{bmatrix},$$

$x^d(t) = [P_{lv}^d\ P_{la}^d\ P_{sa}^d]^T$ represents a desired state corresponding to the healthy cardiovascular system, $$\tilde{A}(t) = A(t)\big|_{\tilde{R}_s, \tilde{c}_{lv,d}}, \text{ and } \tilde{G}(x,t) = G(x,t)\big|_{\tilde{c}_{lv,d}}.$$

7. A system (100) for enhancing cardiac output (CO) in a subject having Mitral Stenosis (MS), the system comprising:
one or more data storage devices (102) operatively coupled to one or more hardware processors (104) and configured to store instructions configured for execution via the one or more hardware processors serving as a first controller, a second controller, a third controller and an adaptive controller comprising a hemodynamic cardiovascular system (CVS) model representative of the subject having MS-to:
receive via the first controller, an error e1 between an actual left ventricular pressure $P_{lv}$ obtained from the adaptive controller comprising the hemodynamic CVS model and a desired left ventricular pressure $P_{lv}^d$, wherein the desired left ventricular pressure corresponds to a healthy cardiovascular system;
generate an updated left ventricle end diastolic compliance $\tilde{c}_{lv,d}$ via the first controller, by minimizing the error e1;
receive via the second controller, an error e2 between an actual aortic pressure $P_{sa}$ obtained from the adaptive controller comprising the hemodynamic CVS model and a desired aortic pressure $P_{sa}^d$, wherein the desired aortic pressure corresponds to the healthy cardiovascular system;
generate an updated systemic vascular resistance $\tilde{R}_s$, via the second controller, by minimizing the error e2;
receive, via the third controller, the updated left ventricle end diastolic compliance $\tilde{c}_{lv,d}$ and the updated systemic vascular resistance $\tilde{R}_s$ to generate control inputs $u_1$ and $u_2$ for opening and closing a mitral valve and an aortic valve respectively of the subject;
receive, via the adaptive controller comprising the hemodynamic CVS model, the updated left ventricle end diastolic compliance $\tilde{c}_{lv,d}$, the updated systemic vascular resistance $\tilde{R}_s$ and the generated control inputs $u_1$ and $u_2$; and
enhance, via the one or more hardware processors serving as the first controller, the second controller and the third controller, the CO in the subject having MS by using the generated control inputs $u_1$ and $u_2$ and adaptively controlling via the hemodynamic CVS model, the parameters of updated left ventricle end diastolic compliance $\tilde{c}_{lv,d}$, and the updated systemic vascular resistance $\tilde{R}_s$ by neuromodulation.

8. The system of claim 7, wherein the updated left ventricle end diastolic compliance $\tilde{c}_{lv,d}$ is based on the actual left ventricular pressure $P_{lv}$, a rate of change of the desired left ventricular pressure $\dot{P}_{lv}^d$ and a diastolic time duration $T-T_s$, and wherein T represents duration of a cardiac cycle having a systolic duration $T_s$, such that the $\tilde{c}_{lv,d}$ is limited to a physiological acceptable range for left ventricle end diastolic compliance $[c_{lv,d}^{min}, c_{lv,d}^{max}]$.

9. The system of claim 8, wherein the updated left ventricle end diastolic compliance $\tilde{c}_{lv,d}$ is represented according to the equation $$\tilde{c}_{lv,d} = \begin{cases} c_{lv,d}^{max} & \text{if } \hat{c}_{lv,d} > c_{lv,d}^{max} \\ \hat{c}_{lv,d} & \text{if } c_{lv,d}^{max} \geq \hat{c}_{lv,d} \geq c_{lv,d}^{min} \\ c_{lv,d}^{min} & \text{if } \hat{c}_{lv,d} < c_{lv,d}^{min} \end{cases},$$

and wherein $\hat{c}_{lv,d}$ is an estimated left ventricle end diastolic compliance and is represented according to the equation $$\hat{c}_{lv,d} = \exp\left(-\frac{\dot{P}_{lv}^d(T - T_s)}{P_{lv}}\right).$$

10. The system of claim 7, wherein the updated systemic vascular resistance $\tilde{R}_s$ is based on the actual aortic pressure $P_{sa}$, a rate of change of the desired aortic pressure $\dot{P}_{sa}^{d}$ and a left atrial pressure $P_{la}$, such that the $\tilde{R}_s$ is limited to a physiological acceptable range for systemic vascular resistance $[R_s^{min}, R_s^{max}]$.

11. The system of claim 10, wherein the wherein the updated systemic vascular resistance $\tilde{R}_s$ is represented according to the equation $$\tilde{R}_s = \begin{cases} R_s^{max} & \text{if } \hat{R}_s > R_s^{max} \\ \hat{R}_s & \text{if } R_s^{max} \geq \hat{R}_s \geq R_s^{min} \\ R_s^{min} & \text{if } \hat{R}_s < R_s^{min} \end{cases},$$

wherein $\hat{R}_s$ is an estimated systemic vascular resistance and is represented according to the equation $$\hat{R}_s = -\frac{P_{sa} - P_{la}}{c_{sa}\dot{P}_{sa}^{d}},$$

and wherein $c_{sa}$ is a constant representing a systemic vascular compliance.

12. The system of claim 7, wherein the hemodynamic CVS model is further configured to receive a cascaded control unit $\tilde{u}$ based on the control inputs $u_1$ and $u_2$, wherein the cascaded control unit it is represented in a state space form according to the equation $$\tilde{u} = \tilde{G}^{-1}(\dot{x}^d - \tilde{A}x)|_{R_s = \tilde{R}_s, c_{lv,d} = \tilde{c}_{lv,d}},$$

and wherein $\dot{x} = A(t)x + G(x,t)u$,
$x = [P_{lv} \ P_{la} \ P_{sa}]^T$, $P_{la}$ representing a left atrial pressure,
$u = [u_1 \ u_2]^T$,
A(t) is a state matrix represented as $$\begin{bmatrix} -\frac{\dot{c}_{lv}(t)}{c_{lv}(t)} & 0 & 0 \\ 0 & -\frac{\dot{c}_{la}(t)}{c_{la}(t)} & \frac{1}{c_{la}(t)R_s} \\ 0 & \frac{1}{c_{sa}R_s} & -\frac{1}{c_{sa}R_s} \end{bmatrix},$$

G (x, t) is an input matrix represented as $$\begin{bmatrix} \frac{P_{la} - P_{lv}}{c_{lv}(t)R_{mi}} & -\frac{P_{lv} - P_{sa}}{c_{lv}(t)R_{ao}} \\ -\frac{P_{la} - P_{lv}}{c_{la}(t)R_{mi}} & 0 \\ 0 & \frac{P_{lv} - P_{sa}}{c_{sa}R_{ao}} \end{bmatrix},$$

$x^d(t) = [P_{lv}^d \ P_{la}^d \ P_{sa}^d]^T$ represents a desired state corresponding to the healthy cardiovascular system, $$\tilde{A}(t) = A(t)|_{\tilde{R}_s, \tilde{c}_{lv,d}}, \text{ and } \tilde{G}(x,t) = G(x,t)|_{\tilde{c}_{lv,d}}.$$

13. A computer program product comprising a non-transitory computer readable medium having a computer readable program embodied therein, wherein the computer readable program, when executed on a computing device, causes the computing device to:

receive, via one or more hardware processors serving as a first controller, an error e1 between an actual left ventricular pressure $P_{lv}$ obtained from an adaptive controller comprising a hemodynamic cardiovascular system (CVS) model representative of the subject having MS and a desired left ventricular pressure $P_{lv}^d$, wherein the desired left ventricular pressure corresponds to a healthy cardiovascular system (402);

generate an updated left ventricle end diastolic compliance $\tilde{c}_{lv,d}$ via the first controller, by minimizing the error e1 (404);

receive, via one or more hardware processors serving as a second controller, an error e2 between an actual aortic pressure $P_{sa}$ obtained from the adaptive controller comprising the hemodynamic CVS model and a desired aortic pressure $P_{sa}^d$, wherein the desired aortic pressure corresponds to the healthy cardiovascular system (406);

generate an updated systemic vascular resistance $\tilde{R}_s$, via the second controller by minimizing the error e2 (408);

receive, via one or more hardware processors serving as a third controller, the updated left ventricle end diastolic compliance $\tilde{c}_{lv,d}$ and the updated systemic vascular resistance $\tilde{R}_s$ to generate control inputs $u_1$ and $u_2$ for opening and closing a mitral valve and an aortic valve respectively (410); and receive, via the adaptive controller comprising the hemodynamic CVS model, the updated left ventricle end diastolic compliance $\tilde{c}_{lv,d}$, the updated systemic vascular resistance $\tilde{R}_s$ and the generated control inputs $u_1$ and $u_2$ (412); and enhancing, via the one or more hardware processors serving as the first controller, the second controller and the third controller, the CO in the subject having MS by using the generated control inputs $u_1$ and $u_2$ and adaptively controlling via the hemodynamic CVS model, the parameters of updated left ventricle end diastolic compliance $\tilde{c}_{lv,d}$, and the updated systemic vascular resistance $\tilde{R}_s$ by neuromodulation.

* * * * *